United States Patent
Pesce et al.

(10) Patent No.: US 6,844,430 B2
(45) Date of Patent: *Jan. 18, 2005

(54) ARTICLES COMPRISING CATIONIC POLYSACCHARIDES AND ACIDIC PH BUFFERING MEANS

(75) Inventors: Antonella Pesce, Pescara (IT); Adelia Alessandra Tordone, Pescara (IT); Giovanni Carlucci, Chieti (IT); Achille Di Cintio, Pescara (IT)

(73) Assignee: The Proctor & Gamble Company, Cincinnati, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/238,013

(22) Filed: Sep. 9, 2002

(65) Prior Publication Data

US 2003/0018312 A1 Jan. 23, 2003

Related U.S. Application Data

(63) Continuation of application No. PCT/US01/13158, filed on Apr. 24, 2001.

(51) Int. Cl.$^7$ .......................... C08B 37/08; A61F 13/15; A61F 13/20
(52) U.S. Cl. .......................... 536/20; 604/375; 604/378
(58) Field of Search .................. 536/20, 55.3; 604/375, 604/378; 442/121, 394

(56) References Cited

U.S. PATENT DOCUMENTS

| 5,525,710 A | * | 6/1996 | Unger et al. ............... 536/18.7 |
| 5,599,916 A | * | 2/1997 | Dutkiewicz et al. .......... 536/20 |
| 5,932,495 A | * | 8/1999 | Boney et al. ............... 442/121 |
| 6,383,960 B1 | * | 5/2002 | Everett et al. .............. 442/394 |

FOREIGN PATENT DOCUMENTS

| EP | 0510619 A1 | * 10/1992 | ........... A61F/13/15 |
| EP | 0 811 392 A1 | 12/1997 | |
| GB | 2 292 526 A | 2/1996 | |
| WO | WO 91/12029 A1 | 8/1991 | |
| WO | WO 99/32697 A2 | 7/1999 | |
| WO | WO 99/55393 A1 | 11/1999 | |

OTHER PUBLICATIONS

The Merck Index, Ninth Edition, 1996, p. 300.*

* cited by examiner

*Primary Examiner*—James O. Wilson
*Assistant Examiner*—Ganapathy Krishnan
(74) *Attorney, Agent, or Firm*—Bridget D. Murray; Kevin C. Johnson

(57) ABSTRACT

The present invention relates to articles, preferably disposable absorbent articles like sanitary napkins and pantiliners, which comprise a cationic polysaccharide, typically chitin-based material and/or chitosan material, and an acidic pH buffering means. Such disposable absorbent articles deliver improved odor control performance even upon prolonged wearing time of the articles.

8 Claims, No Drawings

ARTICLES COMPRISING CATIONIC POLYSACCHARIDES AND ACIDIC PH BUFFERING MEANS

CROSS REFERENCE TO RELATED REFERENCES

This is a continuation of International Application PCT/US01/13158 with an International filing date of Apr. 24, 2001.

FIELD OF THE INVENTION

This invention relates to articles, such as disposable absorbent articles, comprising cationic polysaccharides preferably chitosan materials together with an acidic pH buffering means.

BACKGROUND OF THE INVENTION

Whilst the primary focus of absorbent articles, in particular feminine hygienic absorbent articles like sanitary napkins and pantiliners, remains the ability of these articles to absorb and retain fluids, another important area of development in this field is the control of odorous compounds contained within the absorbent articles during their use.

The presence and detection of malodorous compounds from absorbent articles during their use, particularly those associated with menstruation may cause the wearer of these articles embarrassment. Thus, the prevention of the detection of malodor from such articles is highly desirable too.

In use, the absorbent articles are known to acquire a variety of compounds, for example volatile fatty acids (e.g. isovaleric acid), ammonia, amines (e.g. triethylamine), sulphur containing compounds (e.g. mercaptans, sulphides), alcohols, ketones and aldehydes (e.g., furaldehyde) which release unpleasant odors. These compounds may be present in the bodily fluid or may be developed by chemical reactions and/or any fluid degradation mechanisms once the bodily fluid is absorbed into the absorbent article like for example a feminine hygienic absorbent article. In addition bodily fluids usually contain microorganisms and/or enzymes that can also generate malodorous by products as a result of degradation mechanisms like putrefactive degradation, acid degradation, proteins degradation, fat degradation and the like.

Various odor control materials have been disclosed in the art to combat some of the unpleasant odors referred to above. Indeed solutions have been provided that use different technical approaches like masking, i.e., covering the odor with a perfume, or absorbing the odor already present in the bodily fluids and those generated after degradation, or preventing the formation of the odor.

Most of the focus in the prior art is found on the odor absorption technology. Examples of these types of compounds include activated carbons, clays, zeolites, silicates, cyclodextrine, ion exchange resins and various mixture thereof as for example described in EP-A-348 978, EP-A-510 619, WO 91/12029, WO 91/11977, WO 89/02698, and/or WO 91/12030. All of these types of odor control agents are believed to control odor by mechanisms whereby the malodorous compounds and their precursors are physically absorbed by the agents and thereby hinder the exit of the odor from articles like absorbent articles. However, such mechanisms are not completely effective as the formation of the odor itself is not prevented and thus odor detection is not completely avoided. Some of the focus in the prior art has also been on the use of antimicrobial agents.

Thus although these materials provide some control of odors associated with bodily fluids, there still exists a need of further improvement in terms of odor control of malodors which are generated by the human body, or from bodily fluids such as perspiration, urine, faeces, menstrual fluids, vaginal fluids and the like.

It is an object of the present invention to provide articles, especially disposable absorbent articles, which deliver outstanding odor control, especially towards odor typically associated with bodily fluid. More particularly it is an object of the present invention to provide odor control benefits upon prolonged wearing time of an absorbent article.

It has now surprisingly been found that the addition of a pH buffering means on top of cationic polysaccharides enhances the malodor control properties of such cationic polysaccharides. Indeed, the combination of cationic polysaccharides, preferably chitosan materials, with acidic pH buffering means having a pH in the range of from 3.5 to 6.5 is much more effective in controlling odors, particularly those related to bodily exudates and bodily fluid. Thus the present combination is particularly suitable to be used in articles like disposable absorbent articles especially sanitary napkins, pantiliners or diapers.

More particularly, it has been surprising found that the addition of such an acidic pH buffering means on top of chitosan material results in a synergistic effect in terms of odor control. Indeed this combination gives more odor reduction than the odor reduction associated with the use of one of these two classes of ingredients alone at the same total level (either chitosan material alone or the absorbent gelling material alone) in an absorbent article coming into contact with bodily fluids.

Whilst not wishing to be bound by any particular theory, it is believed that the enhanced odor control benefits associated with the addition of acidic pH buffering means to cationic polysaccharides, especially chitosan materials, in an article, especially disposable absorbent article, is due to the ability of the pH buffering means to enhance the cationic character of the cationic polysaccharides and maintain it even under prolonged wearing time of the absorbent article and/or abundant bodily fluid discharge in the absorbent article. Typically the bodily fluids like menses have an initial pH within the range 6.5 to 7. This pH has the tendency to become more and more basic (within the range 7.5–8) upon ageing of the bodily fluid in the absorbent article. Indeed during normal wearing time, the menses discharge undergoes microbial and enzymatic degradation which results in the production of basic malodorous by-products like ammonia, indole. The use of an acidic pH buffering means will provide a more acidic pH environment and maintain it upon ageing of the menses in the article, typically upon prolonged wearing time. Such an acidic environment has the tendency to enhance the cationic properties of the polysaccharides present in the article and maintain these properties even upon prolonged wearing conditions. The cationic properties of the cationic polysaccharides would otherwise, in absence of such acidic pH buffering means, be neutralized due to increased alkalinity associated to bodily fluid.

Without to be bound by any theory, it is believed that it is the cationic properties of the cationic polysaccharides (preferably chitosan materials) that provide the odor control properties of such materials by multiple mechanisms.

Firstly, the odor absorption and retention characteristics of polysaccharides are due to the presence in the polymer structure of ionisable cationic functional groups. These groups are usually ammonium groups, a high proportion of which are in the salt form when the polymer is dry but which undergo dissociation and salvation upon contact with bodily fluid. In the dissociated state, the polymer chain will have a series of functional groups attached to it which groups have the same electric charge (e.g., $—NH_3^+$ $^+H_3N—$) and thus repel one another. This leads to expansion of the polymer structure, which, in turn permits further absorption of odorous molecules and thus the control thereof.

Secondly, the positively charged cationic groups of the polysaccharides will interact with negatively charged anionic function-bearing molecules present in bodily fluids, like the carboxylic groups of proteins or hydroxylic acid bearing entities like short chain acid (e.g., butyric acid). This will result in the formation of tri-dimensional net between cationic polysaccharides and such molecules with anionic groups (gelification of the bodily fluids). This gelification will entrap most odorous molecules (like lipids, acids) thereby controlling malodor.

Thirdly, cationic polysaccharides especially the aminopolysaccharides (chitosan materials) are believed to act as antimicrobial agents. Indeed the polysaccharides with their positively charged cationic groups will interfere with negatively charged surface of microorganism walls, thereby inhibiting the growth of such microorganisms or even killing such microorganisms. These cationic polysaccharides will also interfere with negatively charged surface of enzymes, thereby inactivating the enzymatic activity, which like the microbial activity, are otherwise responsible for the generation of malodorous components. The cationic polysaccharides like chitosan-based materials further act by their indirect antimicrobial activity by linking some of the microorganism nutriments like lipids and/or minerals.

Advantageously the addition of the pH buffering means as described herein, also results in improved safety and skin properties of the cationic polysaccharides, especially chitosan materials. Indeed, enhancing the cationic properties of chitosan materials translates in enhancing the binding to the negatively charged surface of the skin, in the case of rewetting occurrence (where chitosan can be brought in contact with the skin trough bodily fluid transport), thereby moisturizing the skin and providing a long lasting softness and fullness.

In a preferred embodiment herein the disposable absorbent articles herein have an apertured polymeric film topsheet. This topsheet contributes to further improve the odor control benefit.

In another preferred embodiment herein the disposable absorbent articles herein have a breathable backsheet. This contributes to a further improved odor control benefit. Even more preferred herein the disposable absorbent articles have both a breathable backsheet and an apertured polymeric film topsheet.

The present invention is preferably directed to disposable absorbent articles like pantiliners, feminine napkins, incontinent pads, diapers, tampons, interlabial pads, perspiration pads, surgical pads, breast pads, human or animal waste management devices and the like. Other articles suitable for use according to the present invention further include articles designed to be contacted with the body such as clothing, bandages, thermal pads, acne pads, cold pads, compresses, surgical pads/dressings and the like, body cleansing articles like impregnated wipes/tissues (e.g. baby wipes, wipes for feminine intimate hygiene), articles for absorbing perspiration such as shoe insoles, shirt inserts, and the like, and articles for animals like litters and the like.

BACKGROUND ART

WO99/61079 discloses odor reduction for products such as disposable diapers and training pants, sanitary napkins and tampons by the use of triglycerides and polyglycosides to enhance the malodor absorption properties of compositions and substrates such as naturally occurring polymers like chitosan or alginates and synthetic polymers treated with surfactants.

WO99/32697 discloses that chitosan and chitin-based polymers exhibit increased antimicrobial activity when coated onto the surface of a hydrophobic material such as polypropylene.

None of these references discloses absorbent articles comprising cationic polysaccharides, typically chitosan materials, together with an acidic pH buffering means, let alone that the presence of such an acidic pH buffering means enhances the odor controlling properties of such cationic polysaccharides and maintains them upon prolonged wearing time of the articles.

SUMMARY OF THE INVENTION

The present invention relates to an article, preferably a disposable absorbent article, comprising a cationic polysaccharide together with an acidic pH buffering means, as an odor control system.

The present invention also encompasses a method of controlling odors associated with bodily fluids and/or bodily exudates wherein said bodily fluids and/or exudates are contacted with an odor control system comprising a cationic polysaccharide and an acid pH buffering means.

DETAILED DESCRIPTION OF THE INVENTION

By "article" it is meant herein any three-dimensional solid material being able to comprise a cationic polysaccharide and an acidic pH buffering means. The term "disposable" is used herein to describe articles, which are not intended to be launched or otherwise restored or reused as an article (i.e., they are intended to be discarded after a single use and, preferably to be recycled, composted or otherwise disposed of in an environmentally compatible manner). The term "absorbent articles" is used herein in a very broad sense including any article able to receive and/or absorb and/or contain and/or retain fluids and/or exudates, especially bodily fluids and/or exudates.

Preferred articles according to the present invention are disposable absorbent articles that are designed to be worn in contact with the body of a user and to receive fluids/exudates from the body, such as pantiliners, sanitary napkins, catamenials, incontinence inserts/pads, diapers, tampons, interlabial pads/inserts, breast pads, human or animal waste management devices and the like. Typically such human urine or faecal management devices comprise a bag having an aperture and a flange surrounding the aperture for preferably adhesive attachment to the urogenital area and/or the perianal area of a wearer. Any faecal or urine management device known in the art is suitable for use herein. Such devices are described in for example WO 99/00084 to WO 99/00092. Other suitable articles according to the present invention also include other articles designed to be placed against or in proximity to the body such as clothing, bandages, thermal pads, acne pads, cold pads, compresses, surgical pads/dressings and the like, articles for absorbing perspiration such as shoe insoles, shirt inserts, perspiration pads and the like, body cleansing articles like impregnated wipes/tissues (e.g. baby wipes, wipes for feminine intimate hygiene), and the like, and articles for animals like litters and the like.

By "bodily fluid and/or bodily exudate" it is meant herein any exudate/fluid produced by human or animal body occurring naturally or accidentally like for instance in the case of skin cutting, including for instance perspiration, urine, menstrual fluids, faeces, vaginal secretions and the like.

Cationic Polysaccharides

According to the present invention the articles comprise as an essential component a cationic polysaccharide or a mixture thereof.

Suitable cationic polysaccharides for use herein are positively charged polysaccharides due to the presence of cationic functional groups. Suitable polysaccharides for use herein include natural and semi-synthetic cationic polysaccharides. Suitable for use herein are any aminopolysaccharide-based polymer with cationic amino functional groups. Examples of suitable cationic functional groups include primary, secondary or tertiary amine groups or quaternary ammonium groups, which should be present in, base form. Preferably quaternary ammonium groups are present. The cationic polysaccharides for use herein might be a fibrous polysaccharide such as cellulose with an excess of quaternary ammonium compound containing at least one group capable of reacting with polysaccharide hydroxyl groups. Such cationic polysaccharides are described in WO 92/19652 and WO 96/17681. Highly preferred herein are aminopolysaccharides namely chitin-based materials, chitosan materials, aminocellulose and mixture thereof.

By 'chitosan material' it is meant herein chitosan, modified chitosans, crosslinked chitosan and chitosan salts.

Chitosan is an aminopolysaccharide usually prepared by deacetylation of chitin (poly-beta(1,4)-N-acetyl-D-glucosamine).

Chitin occurs widely in nature, for example, in the cell walls of fungi and the hard shell of insect and crustaceans. The waste from shrimp-, lobster-, and crab seafood industries typically contains about 10 to about 15 percent chitin and is a readily available source of supply. In the natural state, chitin generally occurs only in small flakes or short fibrous material, such as from the carapace or tendons of crustaceans. There is generally no source, as with cotton in the cellulosics, that forms useful shaped articles without solution and re-precipitation or re-naturing.

More specifically, chitin is a mucopolysaccharide, poly-N-acetyl-D-glucosamine with the following formula:

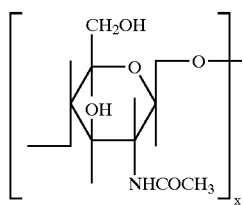

wherein x represents the degree of polymerization. Although x cannot be determined precisely, x is believed to be commonly in the range of from about 50 to about 50,000.

When many of the acetyl groups of chitin are removed by treatment with strong alkalis, the product is chitosan, a high molecular weight linear polymer of 2-deoxy-2-amino glucose.

Chitosan is not a single, definite chemical entity but varies in composition depending on the conditions of manufacture. It may be equally defined as chitin sufficiently deacetylated to form soluble amine salts.

The chitosan used herein is suitably in relatively pure form. Methods for the manufacture of pure chitosan are well known. Generally, chitin is milled into a powder and demineralized with an organic acid such as acetic acid. Proteins and lipids are then removed by treatment with a base, such as sodium hydroxide, followed by chitin deacetylation by treatment with concentrated base, such as 40 percent sodium hydroxide. The chitosan formed is washed with water until the desired pH is reached.

The properties of chitosan relate to its polyelectrolyte and polymeric carbohydrate character. Thus, it is generally insoluble in water, in alkaline solutions at pH levels above about 6.5, or in organic solvents. It generally dissolves readily in dilute solutions of organic acids such as formic, acetic, tartaric, glycolic, lactic and citric acids, and also in dilute mineral acids, except, for example, sulfuric acid. In general, the amount of acid required to dissolve chitosan is approximately stoichiometric with the amino groups. Since the pKa for the amino groups present in chitosan is between 6.0 and 7.0, they can be protonated in very dilute acids or even close to neutral conditions, rendering a cationic nature to this biopolymer. This cationic nature is the basis of many of the benefits of chitosan. Indeed, chitosan material can be considered as a linear polyelectrolyte with a high charge density which can interact with negatively charged surfaces, like proteins (e.g., by interfering with the proteinic wall construction of microorganisms, thereby acting as an antimicrobial agent and/or by reacting with the proteins present in bodily fluid, like menses, thereby acting as a gelifying agent for such fluid) or like anionic absorbent gelling materials that might be present in the articles herein as an optional ingredient (e.g., in a preferred embodiment of the present invention, thereby further enhancing the odor control properties of the cationic polysaccharides and providing outstanding absorption properties even in presence of electrolyte-containing solutions).

Preferred chitosan materials for use herein have an average degree of deacetylation (D.A.) of more than 75%, preferably from 80% to about 100%, even more preferably from 90% to 100% and most preferably from 95% to about 100%. The degree of deacetylation refers to the percentage of the amine groups that are deacetylated. This characteristic is directly related to the hydrogen bonding existing in this biopolymer, affecting its structure, solubility and ultimately its reactivity. The degree of deacetylation can be determined by titration, dye adsorption, UV-VIS, IR, and NMR spectroscopy.

The degree of deacetylation will influence the cationic properties of chitosan material. By increasing the degree of deacetylation the cationic character of chitosan materials will increase and thus their antimicrobial properties, absorbing ability and gelifying ability.

Suitable chitosan materials to use herein include both water-soluble and water insoluble chitosan. As used herein, a material will be considered to be water-soluble when it substantially dissolves in excess water to form a clear and stable solution, thereby, losing its initially particulate form and becoming essentially molecularly dispersed throughout the water solution. Particularly suitable chitosan materials for use herein are water soluble, i.e., at least 0.5 gram, preferably at least 1 gram and most preferably at least 2 grams of the chitosan materials are soluble in 100 grams of water at 25° C. and one atmosphere. By "solubility" of a given compound it is to be understood herein the amount of said compound solubilised in de-ionized water at 25° C. and one atmosphere in absence of precipitate.

As a general rule, the water-soluble chitosan materials will be free from a substantial degree of crosslinking, as crosslinking tends to render the chitosan materials water insoluble.

Water-soluble chitosan materials as defined herein have the benefit to be more active in terms of odor control towards most of the malodorous compounds, present and soluble in the bodily fluid. Indeed such water-soluble chitosan materials have the ability to absorb and/or electrostatically interfere with water-soluble malodorous components like short chain acid (e.g., butyric acid) or low molecular weight alcohol (e.g., ethanol).

Chitosan materials (i.e., chitosan and chitosan salts, modified chitosans and cross-linked chitosans) may generally have a wide range of molecular weights. Chitosan materials with a wide range of molecular weights are suitable for use in the present invention, typically chitosan materials for use herein have a molecular weight ranging from 1 000 to 10 000 000 grams per gram moles and more preferably from 2 000 to 1000 000. Molecular weight means weight average molecular weight. Methods for determining the weight average molecular weight of chitosan materials are known to those skilled in the art. Typical methods include for example light scattering, intrinsic viscosity and gel permeation chromatography. It is generally most convenient to express the molecular weight of a chitosan material in terms of its viscosity in a 1.0 weight percent aqueous solution at 25° C. with a Brookfield viscometer. It is common to indirectly measure the viscosity of the chitosan material by measuring the viscosity of a corresponding chitosan salt, such as by using a 1.0 weight percent acetic acid aqueous solution. Chitosan materials suitable for use in the present invention will suitably have a viscosity in a 1.0 weight percent aqueous solution at 25° C. of from about 1 mPa s (1 centipoise) to about 80,000 mPa s (80,000 centipoise), more suitably from about 30 mPa s (30 centipoise) to about 10,000 mpa·s (10,000 centipoise), even more suitably from 50 mpa·s (50 centipoise) to about 1,000 mPa s (1,000 centipoise) and most suitably from 100 mpa·s (100 centipoise) to about 500 mPa·s (500 centipoise).

Chitosan materials pH depends on the preparation of the chitosan materials. Preferred chitosan materials for use herein have an acidic pH, typically in the range of 4 to 6, more preferably from 4 to 5.5 and even more preferably from 4.5 to 5.5. Highly preferred pH is around pH 5, which corresponds to the skin pH. By pH of chitosan material it is meant herein the pH of a 1% chitosan solution (1 gram of chitosan material dissolved in 100 grams of distilled water) measured by pH-meter.

The cationic properties of the chitosan materials and thus their antimicrobial, absorbing ability and gelifying ability increase with their acidic character. However too high acidity is detrimental to skin safety. Thus it is highly preferred herein to use chitosan materials with a pH in the range of 4.5 to 5.5, thereby delivering the best compromise between odor control and fluid handling properties on one side and skin compatibility on the other side.

Particularly suitable aminopolysaccharides for use herein include aminopolysaccharide salts, especially chitosan salts. A variety of acids can be used for forming aminopolysaccharide salts like chitosan salts. Suitable acids for use are soluble in water or partially soluble in water, are sufficiently acidic to form the ammonium salt of the aminopolysaccharide and yet not sufficiently acidic to cause hydrolysis of the aminopolysaccharide, and are present in amount sufficient to protonate the reactive sites of the deacetylated aminopolysaccharide.

Preferred acids can be represented by the formula:

R—(COOH)$_n$ 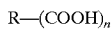

wherein n has a value of 1 or 2 or 3 and R represents a mono- or divalent organic radical composed of carbon, hydrogen and optionally at least one of oxygen, nitrogen and sulfur or R is simply a hydroxyl group. Preferred acids are the mono- and dicarboxylic acids composed of carbon, hydrogen, oxygen and nitrogen (also called herein after amino acids). Such acids are highly desired herein as they are biologically acceptable for use against or in proximity to the human body. Illustrative acids, in addition to those previously mentioned include, among others, citric acid, formic acid, acetic acid, N-acetylglycine, acetylsalicylic acid, fumaric acid, glycolic acid, iminodiacetic acid, itaconic acid, lactic acid, maleic acid, malic acid, nicotinic acid, 2-pyrrolidone-5-carboylic acid, salicylic acid, succinamic acid, succinic acid, ascorbic acid, aspartic acid, glutamic acid, glutaric acid, malonic acid, pyruvic acid, sulfonyldiacetic acid, benzoic acid, epoxysuccinic acid, adipic acid, thiodiacetic acid and thioglycolic acid. Any aminopolysaccharide salt, especially chitosan salts formed from the reaction of the aminopolysaccharide with any of these acids are suitable for use herein.

Examples of chitosan salts formed with an inorganic acid include, but are not limited to, chitosan hydrochloride, chitosan hydrobromide, chitosan phosphate, chitosan sulphonate, chitosan chlorosulphonate, chitosan chloroacetate and mixtures thereof. Examples of chitosan salts formed with an organic acid include, but are not limited to, chitosan formate, chitosan acetate, chitosan lactate, chitosan glycolate, chitosan malonate, chitosan epoxysuccinate, chitosan benzoate, chitosan adipate, chitosan citrate, chitosan salicylate, chitosan propionate, chitosan nitrilotriacetate, chitosan itaconate, chitosan hydroxyacetate, chitosan butyrate, chitosan isobutyrate, chitosan acrylate, and mixtures thereof. It is also suitable to form a chitosan salt using a mixture of acids including, for example, both inorganic and organic acids.

Preferred aminopolysaccharide salts, and especially chitosan salts for use herein are those formed by the reaction of aminopolysaccharides with an amino acid. Amino acids are molecules containing both an acidic and amino functional group. The use of amino acids is highly preferred as those aminopolysaccharide amino salts have higher skin compatibility. Indeed most of the amino acids are naturally present on the skin and thus are non-irritating. Chitosan salts of pyrrolidone carboxylic acid are effective moisturizing agents and are non-irritating to skin. Such chitosan materials are suitable in case of accidental low rewetting occurrence and/or misuse of the articles.

Amino acids for use herein include both linear and/or cyclo amino acids. Examples of amino acids for use herein include, but are not limited to, alanine, valine, leucine, isoleucine, prolinephenylalanine, triptofane, metionine, glycine, serine, cysteine, tyrosine, asparagine, glutamine, aspartic acid, glutamic acid, lysine, arginine, istydine, hydroxyproline and the like. A particularly suitable example of cyclo amino acid is pyrrolidone carboxylic acid, which is a carboxylic acid of pyrrolidin-2-one as per following formula:

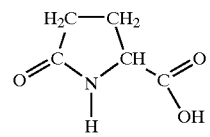

Highly preferred chitosan salts are chitosan pyroglutamate salt, which is a mixture of chitosan (a macromolecule) and pyroglutamic acid (independent monomers), chitosonium pyrrolidone carboxylate, which is the chitosan salt of 2-pyrrolidone-5-carboxylic acid.

Reference is made to WO98/07618, which describes in details processes for the preparation of such aminopolysaccharide salts.

Other aminopolysaccharide materials suitable for use herein include cross-linked aminopolysaccharides and modified aminopolysaccharides, especially cross-linked chitosans and modified chitosans.

Suitable crosslinking agents for use herein are organic compounds having at least two functional groups or functionalities capable of reacting with active groups located on the aminopolysaccharide, typically chitosan materials. Examples of such active groups include, but are not limited to, carboxylic acid (—COOH), or hydroxyl (—OH) groups. Examples of such suitable crosslinking agents include, but are not limited to, diamines, polyamines, diols, polyols, dicarboxylic acids, polycarboxylic acids, aminocarboxylic acids, aminopolycarboxylic acids, polyoxides and the like. One way to introduce a crosslinking agent with the chitosan solution is to mix the crosslinking agent with chitosan during preparation of the solution. Another suitable crosslinking agent comprises a metal ion with more than two positive charges, such as $Ca^{2+}$, $Al^{3+}$, $Fe^{3+}$, $Ce^{3+}$, $Ce^{4+}$, $Ti^{4+}$, $Zr^{4+}$, and $Cr^{3+}$. Since the cations on chitosan possess antimicrobial properties, it is preferred herein to not use a crosslinking agent reacting to the cations, unless no alternative crosslinking agent is available.

In the embodiment herein where crosslinking agents are used, a suitable amount of crosslinking agent is from 0.001 to 30 weight percent based on the total dry weight of chitosan used to prepare the crosslinked-chitosan, more specifically from 0.02 to 20 weight percent, more specifically from 0.05 to 10 weight percent and most preferably from 0.1 to 5 weight percent.

Modified chitosans or chitins for use herein are any chitosan or chitin where the glucan chains carry pendant groups. Examples of such modified chitosans include carboxymethyl chitosan, methyl pyrrolidinone chitosan, glycol chitosan and the like. Methyl pyrrolidone chitosan is for instance described in U.S. Pat. No. 5,378,472, incorporated herein by reference. Water-soluble glycol chitosan and carboxymethyl chitosan are for instance described in WO 87/07618, incorporated herein by reference.

Particularly suitable modified chitosans for use herein include water-soluble covalently bonded chitosan derivatives or ionically bonded chitosan derivatives obtained by contacting salt of chitosan with electrophilic organic reagents. Such water-soluble chitosan derivatives are described in EP-A737 692, which is herein incorporated by reference.

Suitable electrophilic organic reagents suitable for use for the preparation of chitosan derivatives contain from 2 to 18 carbon atoms or more per molecule and typically from 2 to 10 carbon atoms per molecule. In addition the electrophilic organic reagents contain groups, which are reactive, i.e. capable of forming a covalent bond with a nucleophile. Typical electrophilic organic reagents include, for example, ethylene oxide, propylene oxide, butylene oxide, glycidol, 3-chloro-1,2-propanediol, methyl chloride, ethyl chloride, isatoic anhydride, succinic anhydride, octenylsuccinic anhydride, acetic anhydride, gamma-butyrolactone, b-propiolactone, 1,3-propanesultone, acrylamide, glycidyltrimethyl ammonium chloride, glycidyldimethyl alkylammonium chloride such as lauryl, sodium chlorosulfonate, dimethyl sulfate, sodium chloroethanesulfonate, monochloroacetic acid, alkyl phenyl glycidyl ethers, glycidyl trimethoxysilanes, 1,2-epoxy dodecane. One preferred class of electrophilic organic reagent includes those electrophilic organic reagents, which contain an epoxide group, at least one acid group, preferably a diacid group and have from 3 to 18, preferably from 3 to 6 carbon atoms per molecule. Other preferred electrophilic organic reagents include cis-electrophilic organic reagents and trans-electrophilic organic reagent, with cis-electrophilic organic reagents being especially preferred. The electrophilic organic reagent may react with either the free amine or the underivatized hydroxyl groups of the chitosan. It is known that the amine functionality of the chitosan is generally regarded as a stronger nucleophilic site than the hydroxyl groups. Consequently weaker electrophiles will tend to react more readily with the amine groups than with the hydroxyl groups of the chitosan.

Preferably an effective amount of electrophilic organic reagent is substituted onto the chitosan to achieve the desired properties of the chitosan derivative, namely its water-soluble properties. Typically the chitosan derivatives suitable for use herein (modified chitosan) have a MS of from 0.03 to 10 moles of the electrophilic organic reagent per mole of glucosamine monomer unit. The term molar substitution (MS), means the moles of electrophilic organic reagent substituted on the chitosan per mole of glucosamine monomer unit.

In addition further modified chitosan can be prepared which contain other substituent groups, such as hydroxalkyl ether group (e.g., hydroxyethyl or hydroxypropyl ether groups), carboxyalkyl ether groups (e.g., carboxymethyl group), amide groups (e.g., succinyl groups), ester groups (e.g., acetate groups) or amino groups (e.g., 3-(trimethylammonium chloride)-2-hydroxylpropyl or 3-(dimethyloctadecylammonium chloride)-2-hydroxpropyl ether groups) in addition to the electrophilic organic reagent groups. These other substituent groups may be introduced prior to or subsequent to the reaction with the electrophilic organic reagent, or introduced simultaneously by reaction of the chitosan salt with the electrophilic organic reagent and the other derivatizing reagent.

Typically such covalently bonded chitosan derivative might be obtainable by a process which includes the step of (a) dispersing a salt of chitosan (e.g., any one of those described herein before) in an effective amount of an aqueous caustic medium to form a neutralized chitosan containing free amine groups, (b) introducing an electrophilic organic reagent in the slurry and (c) maintaining the slurry at a temperature and time effective to promote the substitution of the electrophilic organic reagent onto the chitosan to form a covalently bonded chitosan derivative and the dissolution of the covalently bonded chitosan into the aqueous medium. The chitosan derivatives can be prepared in either salt form, i.e., ionically bonded, or in the covalently bonded form. Processes for the preparation of such chitosan derivatives are described in depth in EP-A-737 692, incorporated herein by reference.

Suitable chitosans are commercially available from numerous vendors. Exemplary of a commercially available chitosan materials are those available from for example the Vanson Company. The preferred chitosan salt for use herein is chitosan pyrrolidone carboxylate (also called chitosonium pyrrolidone carboxylate), which has a degree of deacetylation more than 85%, a water solubility of 1% (1 gram is soluble in 100 grams of distilled water at 25° C. and one atmosphere), a pH of 4.5 and a viscosity between 100–300 cps. Chitosan pyrrolidone carboxylate is commercially available under the name Kytamer® PC from Amerchol Corporation.

Typically, the articles like disposable absorbent articles comprise cationic polysaccharide or a mixture thereof at a level of from 0.5 gm$^{-2}$ to 500 gm$^{-2}$, preferably from 1 to 200 gm$^{-2}$, more preferably from 3 gm$^{-2}$ to 100 gm$^{-2}$ and most preferably from 4 gm$^{-2}$ to 50 gm$^{-2}$ As used herein, "gm$^{-2}$" and "g/m$^2$" are used synonymously as abbreviations for grams per meter suuared.

The pH Buffering Means

According to the present invention the articles comprise as an essential component an acidic pH buffering means or a mixture thereof.

By "pH buffering means", it is meant herein any compound which when added to a solution makes the solution to resist to a change in hydrogen ion concentration on addition of acid or alkali.

Preferred pH buffering means for use herein are acidic pH buffering means having a pH in the range of from 3.5 to 6.5, i.e., that the pH buffering means for use herein comprise a weak acid having its pKa (if only one) or at least one of its pKas in the range from 3.5 to 6.5, preferably from 4 to 6 and more preferably from 5 to 6, and its conjugated base.

pK$_a$ is defined according to the following equation:

$$pK_a = -\log K_a$$

where $K_a$ is the Dissociation Constant of the weak acid in water and corresponds to the following equation:

$$[A^-][H^+]/[HA] = K_a$$

where HA is the acid and A$^-$ is the conjugated base.

By "conjugated base", it is meant herein the corresponding base (A$^-$) of the weak acid herein (HA). This conjugate base may be obtained by adding a source of alkalinity to the weak acid as defined herein. Suitable source of alkalinity suitable for use herein are the caustic alkalis such as sodium hydroxide, potassium hydroxide and/or lithium hydroxide and/or the alkali metal oxides such as sodium and/or potassium oxide. A preferred source of alkalinity is a caustic alkali, more preferably sodium hydroxide and/or potassium hydroxide. Alternatively the conjugate base may be commercially available per se and added directly to the weak acid herein.

Typically, according to the present invention the weak acid (HA) and its conjugate base (A$^-$) are in equilibrium according to the equation:

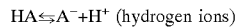
$$HA \rightleftharpoons A^- + H^+ \text{ (hydrogen ions)}$$

Typically the pH buffering means herein consists of a weak acid as defined herein and its conjugate base at a weight ratio of the weak acid to its conjugate base of preferably 0.1:1 to 10:1, more preferably 0.2:1 to 5:1. Highly preferred ratio of the weak acid to its conjugate base is 1 since this is the best combination to achieve optimum buffering capacity.

Preferably a given pH buffering means herein will be used to buffer mediums having a pH between pH=pKa−1 and pH=pKa+1 of each of its pKa. For example citric acid/citrate is particularly suitable to buffer mediums having a pH comprised between 3.74 and 5.74 (pKa 2=4.74). Bodily fluid discharges like perspiration, menses, and urine have an initial pH ranging between 5–6.5. Upon aging of the fluids in the absorbent article, the pH of the bodily fluids has the tendency to become more and more alkaline as a result of the degradative activity of microorganisms. The bodily fluids will be acidified and buffered by the acidic pH buffering means.

Suitable weak acids having at least one of their pK$_a$s of from 3.5 to 6.5 for use herein include citric acid (pKa=1= 3.06, pKa 2=4.74), oxalic acid (pKa 2=4.19), tartaric acid (pKa 1=2.99, pKa 2=4.34), phtalic acid (pKa 1=2.89, pKa 2=5.41), acetic acid (pKa=4.74), benzoic acid (pKa=4.20), glutaric acid (pka1=4.34, pKa2=5.22), adipic acid (pka1= 4.4, pka2=5.28) and/or carbonic acid (pka=3.8).

Particularly suitable pH buffering means for use herein are citric acid/sodium hydroxide, citric acid/sodium citrate, citric acid/potassium citrate, oxalic acid/sodium oxalate, tartaric acid/potassium hydrogen tartarate, oxalic acid/ potassium tetra oxalate dihydrate, phtalic acid/potassium phtalate, phtalic acid/sodium phtalate acetic acid/sodium acetate, benzoic acid/sodium benzoate, glutaric acid/sodium glutarate, adipic acid/sodium adipate, carbonic acid/sodium carbonate or mixture thereof. Preferred pH buffering means for use herein are citric acid/sodium citrate, citric acid/ potassium citrate, citric acid/sodium hydroxide, oxalic acid/ sodium oxalate, tartaric acid/potassium hydrogen tartarate, oxalic acid/potassium tetra oxalate dihydrate, and most preferred is citric acid/sodium citrate, citric acid/sodium hydroxide and/or citric acid/potassium citrate.

Highly preferred pH buffering means for use herein is citric acid and sodium hydroxide.

Citric acid/sodium hydroxide is commercially available from Sigma Aldrich under trade name Fixanal®.

Typically, the articles like disposable absorbent articles comprise the acidic pH buffering means at a level of from 0.1 gm$^{-2}$ to 250 gm$^{-2}$, preferably from 1 to 150 gm$^{-2}$, more preferably from 10 gm$^{-2}$ to 100 gm$^{-2}$ and most preferably from 30 gm$^{-2}$ to 80 gm$^{-2}$.

Optional Agents

The articles according to the present invention preferably further comprise on top of the cationic polysaccharides and the acid pH buffering means, optional conventional agents or mixtures thereof.

Absorbent Gelling Odor Control Materials

According to the present invention the articles comprise as an optional component an absorbent gelling material (sometimes referred to as "super-sorber").

Particularly preferred absorbent gelling materials for use herein are anionic absorbent gelling materials, i.e., absorbent gelling materials that are predominantly negatively charged. These absorbent gelling materials can be any material having superabsorbent properties in which the functional groups are anionic, namely sulphonic groups, sulphate groups, phosphate groups or carboxyl groups. Preferably the functional groups are carboxyl groups. Particularly preferred anionic absorbent gelling materials for use herein are synthetic anionic absorbent gelling materials. Synthetic anionic absorbent gelling materials are preferred herein as they deliver higher odor and fluid absorption performance, this even under pressure, as compared to the absorption performance associated with natural anionic absorbent gelling materials like anionic polysaccharides when used in the same absorbent article.

Generally the functional groups are attached to a slightly cross-linked acrylic base polymer. For example the base polymer may be a polyacrylamide, polyvinyl alcohol, ethylene maleic anhydride copolymer, polyvinylether, polyvinyl sulphonic acid, polyacrylic acid, polyvinylpyrrolidone and polyvinylmorpholine. Copolymers of these monomers can also be used. Particular base polymers include cross-linked polyacrylates, hydrolyzed acrylonitrile grafted starch, starch polyacrylates and isobutylene maleic anhydride copolymers.

Such materials form hydrogels on contact with water (e.g., with urine, blood, and the like). One highly preferred type of hydrogel-forming, absorbent gelling material is based on polyacids, especially polyacrylic acid. Hydrogel-forming polymeric materials of this type are those, which, upon contact with fluids (i.e., liquids) such as water or body fluids, imbibe such fluids and thereby form hydrogels. These preferred absorbent gelling materials will generally comprise substantially water-insoluble, slightly cross-linked, partially neutralized, hydrogel-forming polymer materials prepared from polymerisable, unsaturated, acid-containing monomers. In such materials, the polymeric component formed from unsaturated, acid-containing monomers may comprise the entire gelling agent or may be grafted onto other types of polymer moieties such as starch or cellulose. Acrylic acid grafted starch materials are of this latter type. Thus, the preferred absorbent gelling materials include hydrolyzed acrylonitrile grafted starch, acrylic acid grafted starch, polyacrylates, maleic anhydride-based copolymers and combinations thereof. Especially preferred absorbent gelling materials are the polyacrylates and acrylic acid grafted starch.

Whatever the nature of the polymer components of the preferred absorbent gelling materials, such materials will in general be slightly cross-linked. Crosslinking serves to render these preferred hydrogel-forming absorbent materials substantially water-insoluble, and cross-linking also in part determines the gel volume and extractable polymer characteristics of the hydrogels formed there from. Suitable cross-linking agents are well known in the art and include, for example, (1) compounds having at least two polymerisable double bonds; (2) compounds having at least one polymerisable double bond and at least one functional group reactive with the acid-containing monomer material; (3) compounds having at least two functional groups reactive with the acid-containing monomer materials; and (4) polyvalent metal compounds which can from ionic cross-linkages. Cross-linking agents of the foregoing types are described in greater detail in Masuda et al; U.S. Pat. No. 4,076,663; Issued Feb. 28, 1978. Preferred cross-linking agents are the di- or polyesters of unsaturated mono-or polycarboxylic acids with polyols, the bisacrylamides and the di-or triallyl amines. Especially preferred cross-linking agents are N,N'-methylenebisacrylamide, trimethylol propane triacrylate and triallyl amine. The cross-linking agent will generally comprise from about 0.001 mole percent to 5 mole percent of the preferred materials. More preferably, the cross-linking agent will comprise from about 0.01 mole percent to 3 mole percent of the gelling materials used herein.

The preferred absorbent gelling materials used herein are those which have a relatively high capacity for imbibing fluids encountered in the absorbent articles; this capacity can be quantified by referencing the "gel volume" of said absorbent gelling materials. Gel volume can be defined in terms of the amount of synthetic urine absorbed by any given absorbent gelling agent buffer and is specified as grams of synthetic urine per gram of gelling agent.

Gel volume in synthetic urine (see Brandt, et al, below) can be determined by forming a suspension of about 0.1–0.2 parts of dried absorbent gelling material to be tested with about 20 parts of synthetic urine. This suspension is maintained at ambient temperature under gentle stirring for about 1 hour so that swelling equilibrium is attained. The gel volume (grams of synthetic urine per gram of absorbent gelling material) is then calculated from the weight fraction of the gelling agent in the suspension and the ratio of the liquid volume excluded from the formed hydrogel to the total volume of the suspension. The preferred absorbent gelling materials useful in this invention will have a gel volume of from about 20 to 70 grams, more preferably from about 30 to 60 grams, of synthetic urine per gram of absorbent gelling material.

Another feature of the most highly preferred absorbent gelling materials relates to the level of extractable polymer material present in said materials. Extractable polymer levels can be determined by contacting a sample of preferred absorbent gelling material with a synthetic urine solution for the substantial period of time (e.g., at least 16 hours) which is needed to reach extraction equilibrium, by then filtering the formed hydrogel from the supernatant liquid, and finally by then determining the polymer content of the filtrate. The particular procedure used to determine extractable polymer content of the preferred absorbent gelling agent buffers herein is set forth in Brandt, Goldman and Inglin; U.S. Pat. No. 4,654,039; Issues Mar. 31, 1987, Reissue 32,649, The absorbent gelling materials which are especially useful in the absorbent articles herein are those which have an equilibrium extractable content in synthetic urine of no more than about 17%, preferably no more than about 10% by weight of the absorbent gelling material.

The preferred, slightly cross-linked, hydrogel-forming absorbent gelling materials will generally be employed in their partially neutralized form. For purposes described herein, such materials are considered partially neutralized when at least 25 mole percent, and preferably at least 50 mole percent of monomers used to form the polymer are acid group-containing monomers, which have been neutralized with a salt-forming cation. Suitable salt-forming cations include alkali metal, ammonium, substituted ammonium and amines. This percentage of the total monomers utilized, which are neutralized acid group-containing monomers, is referred to as the "degree of neutralization". Typically, commercial absorbent gelling materials have a degree of neutralization somewhat from 25% to 90%.

The absorbent gelling materials herein before described are typically used in the form of discrete particles. Such absorbent gelling materials can be of any desired shape, e.g., spherical or semi-spherical, cubic, rod-like polyhedral, etc. Shapes having a large greatest dimension/smallest dimension ratio, like needles and flakes, are also contemplated for use herein. Agglomerates of absorbent gelling material particles may also be used.

The size of the absorbent gelling material particles may vary over a wide range. For reason of industrial hygiene, average particle sizes smaller than about 30 microns are less desirable. Particles having a smallest dimension larger than about 2 mm may also cause a feeling of grittiness in the absorbent article, which is undesirable from a consumer aesthetics standpoint. Furthermore, rate of fluid absorption can be affected by particle size. Larger particles have very much reduced rates of absorption. Preferred for use herein are absorbent gelling material s particles substantially all of which have a particle size of from about 30 microns to about 2 mm. "Particle Size" as used herein means the weighted average of the smallest dimension of the individual particles.

The amount of absorbent gelling material particles used in the article according to the present invention, especially disposable absorbent articles, will typically range from 5 $gm^{-2}$ to 250 $gm^{-2}$, preferably from 7 $gm^{-2}$ to 150 $gm^{-2}$, more preferably from 10 $gm^{-2}$ to 100 $gm^{-2}$.

Anionic absorbent gelling materials are suitably used on top of the cationic polysaccharides and pH buffering means herein as they further contribute to enhance the benefices of the present invention. Indeed the anionic absorbent gelling materials are believed to further enhance the cationic properties of the cationic polysaccharides, thus their odor control properties.

The addition of anionic absorbent gelling materials, namely synthetic anionic absorbent gelling materials as described herein (typically having a degree of neutralization of from 25% to 90%) on top of cationic polysaccharides, especially chitosan materials, in an absorbent article also results in outstanding fluid absorption capacity not only towards water but especially towards electrolytes-containing solutions like menses.

Furthermore the use of anionic absorbent gelling materials, namely synthetic anionic absorbent gelling materials as described herein (typically having a degree of neutralization of from 25% to 90%) on top of cationic polysaccharides, especially chitosan material, in an absorbent article, exhibit high gel strength during fluid absorption. Indeed this combination results in improved absorption capacity under load conditions, in decreased rewetting and wetting through and hence improved comfort.

Advantageously the presence of anionic synthetic absorbent gelling agents on top of the odor control system of the present invention (i.e., cationic polysaccharides and pH buffering means) results in optimum fluid absorption and optimum odor control of malodors typically associated with bodily fluids.

Optional Odor Control Agent

For instance additional odor control agent or combinations thereof, known in the art for this purpose may be used herein. These agents can typically be classified according to the type of odor the agent is intended to combat. Odors may be chemically classified as being acidic, basic or neutral.

Alternatively, the odor control agents may be categorized with respect to the mechanism by which the malodor detection is reduced or prevented. For example, odor control agents which chemically react with malodorous compounds or with compounds which produce malodorous degradation products thereby generating compounds lacking odor or having an odor acceptable to consumers may also be utilized herein.

Suitable odor control agents for use herein typically include activated carbons, clays, zeolites, silicas, diatomaceous earth and cyclodextrine. Such odor control agents and systems are disclosed in more details hereinafter and for example in EP-A-510 619, WO 91/12029, WO 91/11977, WO 91/12030, WO 81/01643 and WO 96/06589.

Suitable odor control agents also include chelating agents and may be selected from amino carboxylates such as for example ethylenediamine-tetracetate, as described for example in U.S. Pat. No. 4,356,190, amino phosphonates such as ethylenediaminetetrakis (methylene-phosphonates), polyfunctionally-substituted aromatic chelating agents as described in U.S. Pat. No. 3,812,044 and mixtures thereof. Without intending to be bound by theory it is believed that the benefit of these materials is in part due to their exceptional ability to remove iron, copper, calcium, magnesium and manganese ions present in the absorbed fluids and their degradation products by the formation of chelates.

Alternative odor control agents are ion exchange resins such as those described in U.S. Pat. No. 4,289,513 and U.S. Pat. No. 3,340,875.

Masking agents such as perfumes may also be used as odor control agents herein.

Typically, the articles like disposable absorbent articles may comprise the additional odor control agent or a mixture thereof at a level of from 0.5 $gm^{-2}$ to 600 $gm^{-2}$, preferably from 5 to 500 $gm^{-2}$, more preferably from 10 $gm^{-2}$ to 350 $gm^{-2}$ and most preferably from 20 $gm^{-2}$ to 200 $gm^{-2}$.

The Absorbent Article

Cationic polysaccharides and acidic pH buffering means may be incorporated into the absorbent article by any of the methods disclosed in the art, for example layered on the core of the absorbent article or mixed within the fibers of the absorbent core.

Cationic polysaccharides and acidic pH buffering means and optional additional odor control agent(s) and/or optional absorbent gelling material are preferably incorporated between two layers of cellulose tissue. Optionally the system may be bonded between two cellulose tissue layers with, for example, a hot melt adhesive or any suitable bonding system, as described in WO 94/01069.

In one embodiment of the present invention the cationic polysaccharide, acidic pH buffering means and/or optional absorbent gelling material and/or optional additional odor control agent are incorporated in a layered structure in accordance with the disclosure of WO 94/01069 or Italian patent application number TO 93A 001028. TO 93A 001028 describes a layered structure substantially as described in WO 94/01069 with the exception that TO 93A 001028 comprises a much higher quantity of absorbent gelling material in the intermediate layer which is between the fibrous layers (120 $gm^{-2}$) that would be incorporated in the present invention as an optional ingredient. The intermediate layer comprises in particular a polyethylene powder as thermoplastic material, which is mixed with the cationic polysaccharide and pH buffering agent and additional optional ingredients. The mixture is then heated such that the polyethylene melts and glues the laminate layers together. Adhesive lines are preferably also placed on the edges of the laminate to ensure that the edges of the laminate stick and any loose cationic polysaccharides, acidic pH buffering means and optional absorbent gelling material and/or optional additional odor control agent present do not fall out of the laminate.

Alternatively, the polyethylene powder may be replaced by a conventional glue for instance those commercially available from ATO Findley under the name H20–31® to glue the laminate layers and/or components together. Advantageously this method step allows to avoid the heating step necessary when using polyethylene powder.

The cationic polysaccharides and acidic pH buffering means may be distributed together or separately, homogeneously or non homogeneously, over the entire absorbent article or in at least one layer of the topsheet and/or backsheet or in at least one layer of the core or any mixture thereof. The cationic polysaccharides and acidic pH buffering means may be distributed homogeneously or non homogeneously on the whole surface of the desired layer or layers, or on one or several area of the surface layer/layers to which it is positioned (e.g. central area and/or surrounding area like the edges of a layer of the absorbent article) or mixtures thereof.

In a preferred embodiment herein, wherein an absorbent gelling material is present, the absorbent gelling material is positioned such that at least a portion of the bodily fluid/exudate comes into contact with said absorbent gelling material before the cationic polysaccharides and pH buffering means. In a highly preferred embodiment herein the absorbent gelling material is located in the core and the cationic polysaccharides typically chitosan material and pH buffering means are located in the core too but further away from the topsheet than the absorbent gelling material and/or in the backsheet. One particular execution is the one where the absorbent core comprises a laminate of two fibrous layers (a first and a second fibrous layer, the first layer facing the topsheet and the second layer facing the backsheet), wherein the absorbent gelling material is distributed between the first and the second layer of the laminate and the cationic polysaccharide and acidic pH buffering means are located onto the second fibrous layer of the laminate (e.g., by spraying a solution of both materials on either the inner or outer surface of said layer or both surfaces). Such executions are particularly beneficial for combining optimum odor control properties with optimum fluid handling, i.e., optimum odor and fluid absorption and retention without any leakage through or rewetting occurrence. The cationic polysaccharide due to its gelifying properties will have the tendency to form a so-called impermeable layer towards the backsheet thereby preventing any leakage through.

The cationic polysaccharides and acidic pH buffering means, the optional absorbent gelling material and/or optional odor control agent if present may be incorporated as a powder, a granulate or can be sprayed in the form of for example a polysaccharide-containing solution and/or citric acid/sodium hydroxide containing solution within the absorbent article. When used in a granulate or particulate form the cationic polysaccharides (e.g., chitosan material) and pH buffering means as well as the optional absorbent gelling material and/or optional odor control agent may be granulated separately and then mixed together or granulated together.

Suitable disposable absorbent articles according to the present invention include those described as follows:

Absorbent Core

According to the present invention, the absorbent can include the following components: (a) an optional primary fluid distribution layer preferably together with a secondary optional fluid distribution layer; (b) a fluid storage layer; (c) an optional fibrous ("dusting") layer underlying the storage layer; and (d) other optional components. According to the present invention the absorbent may have any thickness depending on the end use envisioned.

a Primary/Secondary Fluid Distribution Layer

One optional component of the absorbent according to the present invention is a primary fluid distribution layer and a secondary fluid distribution layer. The primary distribution layer typically underlies the topsheet and is in fluid communication therewith. The topsheet transfers the acquired fluid to this primary distribution layer for ultimate distribution to the storage layer. This transfer of fluid through the primary distribution layer occurs not only in the thickness, but also along the length and width directions of the absorbent product. The also optional but preferred secondary distribution layer typically underlies the primary distribution layer and is in fluid communication therewith. The purpose of this secondary distribution layer is to readily acquire fluid from the primary distribution layer and transfer it rapidly to the underlying storage layer. This helps the fluid capacity of the underlying storage layer to be fully utilized. The fluid distribution layers can be comprised of any material typical for such distribution layers. In particular fibrous layers maintain the capillaries between fibers even when wet are useful as distribution layers.

b Fluid Storage Layer

Positioned in fluid communication with, and typically underlying the primary or secondary distribution layers, is a fluid storage layer. The fluid storage layer can comprise the cationic polysaccharides alone or in combination with any additional usual absorbent gelling material. It preferably comprises the cationic polysaccharides with optionally an absorbent gelling material in combination with suitable carriers.

Suitable carriers include materials, which are conventionally utilized in absorbent structures such as natural, modified or synthetic fibers, particularly modified or non-modified cellulose fibers, in the form of fluff and/or tissues. Most preferred are tissue or tissue laminates in the context of sanitary napkins and panty liners.

An embodiment of the absorbent structure made according to the present invention may comprise multiple layers comprises a double layer tissue laminate typically formed by folding the tissue onto itself. These layers can be joined to each other for example by adhesive or by mechanical interlocking or by hydrogen bridge bands. The cationic polysaccharides and optional absorbent gelling materials and other optional materials can be comprised between the layers.

Modified cellulose fibers such as the stiffened cellulose fibers can also be used. Synthetic fibers can also be used and include those made of cellulose acetate, polyvinyl fluoride, polyvinylidene chloride, acrylics (such as Orlon), polyvinyl acetate, non-soluble polyvinyl alcohol, polyethylene, polypropylene, polyamides (such as nylon), polyesters, bicomponent fibers, tricomponent fibers, mixtures thereof and the like. Preferably, the fiber surfaces are hydrophilic or are treated to be hydrophilic. The storage layer can also include filler materials, such as Perlite, diatomaceous earth, Vermiculite, etc., to improve liquid retention.

If the cationic polysaccharides and optional absorbent gelling materials are dispersed non-homogeneously in a carrier, the storage layer can nevertheless be locally homogenous, i.e. have a distribution gradient in one or several directions within the dimensions of the storage layer. Non-homogeneous distribution can also refer to laminates of carriers enclosing cationic polysaccharides and optionally absorbent gelling materials partially or fully.

c Optional Fibrous ("Dusting") Layer

An optional component for inclusion in the absorbent core according to the present invention is a fibrous layer adjacent to, and typically underlying the storage layer. This underlying fibrous layer is typically referred to as a "dusting" layer since it provides a substrate on which to deposit absorbent gelling material in the storage layer during manufacture of the absorbent core. Indeed, in those instances where the absorbent gelling material is in the form of macro structures such as fibers, sheets or strips, this fibrous "dusting" layer need not be included. However, this "dusting" layer provides some additional fluid-handling capabilities such as rapid wicking of fluid along the length of the pad.

d Other Optional Components of the Absorbent Structure

The absorbent core according to the present invention can include other optional components normally present in absorbent webs. For example, a reinforcing scrim can be positioned within the respective layers, or between the respective layers, of the absorbent core. Such reinforcing scrims should be of such configuration as to not form interfacial barriers to fluid transfer. Given the structural integrity that usually occurs as a result of thermal bonding, reinforcing scrims are usually not required for thermally bonded absorbent structures.

The Topsheet

According to the present invention the absorbent article comprises as an essential component a topsheet. The topsheet may comprise a single layer or a multiplicity of layers. In a preferred embodiment the topsheet comprises a first layer, which provides the user-facing surface of the topsheet and a second layer between the first layer and the absorbent structure/core.

The topsheet as a whole and hence each layer individually needs to be compliant, soft feeling, and non-irritating to the wearer's skin. It also can have elastic characteristics allowing it to be stretched in one or two directions. According to the present invention the topsheet may be formed from any of the materials available for this purpose and known in the art, such as woven and non-woven fabrics and films. In a preferred embodiment of the present invention at least one of the layers, preferably the upper layer, of the topsheet comprises a hydrophobic, liquid permeable apertured polymeric film. Preferably, the upper layer is provided by a film material having apertures, which are provided to facilitate liquid transport from the wearer-facing surface towards the absorbent structure. Such apertured polymeric topsheet further participates to the odor control benefit. If present the lower layer preferably comprises a non-woven layer, an apertured formed film or an air laid tissue.

The Backsheet

The backsheet primarily prevents the extrudes absorbed and contained in the absorbent structure from wetting articles that contact the absorbent product such as underpants, pants, pyjamas and undergarments. The backsheet is preferably impervious to liquids (e.g. menses and/or urine) and is preferably manufactured from a thin plastic film, although other flexible liquid impervious materials can also be used. As used herein, the term "flexible" refers to materials that are compliant and will readily conform to the general shape and contours of the human body. The backsheet also can have elastic characteristics allowing it to stretch in one or two directions.

The backsheet typically extends across the whole of the absorbent structure and can extend into and form part of or all of the preferred side flaps, side wrapping elements or wings.

The backsheet can comprise a woven or nonwoven material, polymeric films such as thermoplastic films of polyethylene or polypropylene, or composite materials such as a film-coated nonwoven material. Preferably, the backsheet is a polyethylene film typically having a thickness of from about 0.012 mm (0.5 mil) to about 0.051 mm (2.0 mil).

Exemplary polyethylene films are manufactured by Clopay Corporation of Cincinnati, Ohio, under the designation P18-0401 and by Ethyl Corporation, Visqueen Division, of Terre Haute, Ind., under the designation XP-39385. The backsheet is preferably embossed and/or matt finished to provide a more cloth like appearance. Further, the backsheet can permit vapors to escape from the absorbent structure, i.e. be breathable, while still preventing exudates from passing through the backsheet. Also breathable backsheets comprising several layers, e.g. film plus non-woven structures, can be used. Breathable may be preferred herein as they contribute to further improve the odor control benefit associated with the present invention. Even more preferred herein the disposable absorbent articles have both a breathable backsheet and an apertured polymeric film topsheet for further increasing the odor control performance of the articles.

Odor Control Test

The odor reduction is measured by for example an in vitro sniff test. In vitro sniff test consists in analyzing by expert graders the odor associated with articles comprising the ingredients to be tested (including references articles) when contacted with an odorous components-containing solution. The expert graders express their judgment about (un) pleasantness of the odor using a (un)pleasantness scale, typically from −10 (highest level of unpleasantness) to 5 (most pleasant). With this procedure, each grader compares MU (Unpleasantness) in the test session. The relative MU odor values from different products are assigned numbers. For example, in a test session, a sample that is perceived to be twice as strong as another is assigned twice as large a number. One that is perceived to be one-tenth as strong as another is assigned a number one-tenth as large, etc. In each test session, zero is used to designate neutral hedonicity, and + and − numbers are assigned in ratio proportion to the relative pleasantness and unpleasantness of the odor.

Surprisingly in vitro in-house sniff tests conducted by using an in-house odorous components-containing solution reproducing the essential malodorous characteristics of menses showed synergistic odor reduction when comparing chitosan material (e.g. chitosonium pyrrolidone carboxylate (Kytamer®) together with an acidic pH buffering means (e.g., citric acid/sodium hydroxide solution (pH 5) at a ratio 1:1 commercially available from Aldrich under the trade name Fixanal®) to each of these ingredients taken alone at the same total level of active. Indeed the % of unpleasantness reduction obtained for the mixture was higher than the % of unpleasantness reduction obtained for each of the two ingredients used alone at the same total level of active. The Unpleasantness values, for each sample, were obtained as a mean of at least 15 observations (3 products, 5 graders). These results were statistically significant.

Alternatively the odor reduction can also be measured with in vivo sniff tests as described in patent applications, EP-A-811387 or WO97/46191, herein incorporated by reference.

The present invention is further illustrated by the following example.

EXAMPLES

Example A

The feminine pads used in the following examples were Always (Always is a registered Trade Mark) as sold by the Procter & Gamble Company.

Each feminine pad was opened by cutting the wrap around the perforated coverstock at its bottom face approximately along a longitudinal edge of the release paper, which covers the external adhesive layer. The side of the absorbent fibrous core was then exposed by slightly shifting the water impermeable plastic bottom layer and subsequently, the fibrous core was split into two halves, each having approximately the same thickness, along a plane, which is parallel to the plane of the napkin itself.

A wet powder was prepared by mixing chitosan powder material and acidic pH buffering means solution at a weight ratio of 1:10. The so obtained wet powder (0.9 g) was homogeneously distributed between these tow fibrous layers, which were then joined together to reconstitute the absorbent core.

The water impermeable inner backsheet was then put back into its original position and the wrap around perforated coverstock was sealed along the cut by means of e.g. a double-sided adhesive tape.

The chitosan powder material used was chitosan pyrrolidone carboxylate, commercially available from Amerchol Corporation, Edison, N.J. under the name Kytamer® PC.

The pH buffering means used was citric acid/sodium hydroxide solution (pH 5) at a ratio 1:1 commercially available from Aldrich under the trade name Fixanal®.

Example B

The feminine pads used in the following examples were Always (Always is a registered Trade Mark) as sold by the Procter & Gamble Company.

Each feminine pad was opened by cutting the wrap around the perforated coverstock at its bottom face approximately along a longitudinal edge of the release paper, which covers the external adhesive layer. The side of the absorbent fibrous core was then exposed by slightly shifting the water impermeable plastic bottom layer and subsequently, the fibrous core was split into two halves, each having approximately the same thickness, along a plane, which is parallel to the plane of the napkin itself.

A chitosan and pH buffering containing solution was prepared by mixing 2 g of chitosan material together with 0.2 g a buffering pH means into 100 g of distilled water. The solution was stirred overnight at room temperature (25° C.). 10 g of the so obtained solution was sprayed onto the lower halve fibrous layer. This fibrous layer was then dried overnight at 40° C. in an oven. Then the tow fibrous layers were joined together to reconstitute the absorbent core. The lower halve of the fibrous layer was joined to the upper halve so that the side on which the chitosan-pH buffering solution was sprayed was inside the absorbent core so obtained. Alternatively the absorbent core can also be reconstituted with the side onto which the chitosan-pH buffering solution has been sprayed directed towards the water impermeable plastic bottom layer (also called backsheet).

The water impermeable inner backsheet was then put back into its original position and the wrap around perforated coverstock was sealed along the cut by means of e.g. a double-sided adhesive tape.

The chitosan powder material used was chitosan pyrrolidone carboxylate, commercially available from Amerchol Corporation, Edison, N.J. under the name Kytamer® PC.

The pH buffering means used was citric acid/sodium hydroxide solution (pH 5) at a ratio of 1:1 commercially available from Aldrich under the trade name Fixanal®.

Example C

Other pads were prepared by following the method in Example A except that an absorbent gelling material (AGM) was homogeneously distributed between the two fibrous layer beside the wet powder of chitosan material in Example A before reconstituting the pad.

The AGM (0.4 g) used was cross-linked sodium polyacrylate XZ 9589001, available from Dow Chemicals.

Example D

Other pads were prepared by following the method in Example B except that an absorbent gelling material (AGM) was homogeneously distributed between the two fibrous layers before reconstituting the pad.

The AGM (0.4 g) used was cross-linked sodium polyacrylate XZ 9589001, available from Dow Chemicals.

Example E

Other pads were prepared by following the method in Example A except that after having split the fibrous core into two halves, AGM was homogeneously distributed onto the upper halve fibrous layer (i.e. the fibrous layer halve intended to be closer to the topsheet) and chitosan and pH buffering means-containing wet powder as defined in example A was homogeneously distributed onto the lower halve fibrous layer (i.e., the one intended to be closer to the backsheet of the pad once reconstituted). Then a layer of air laid tissue (19 mm*70 mm of low basis weight) available from Fripa under the code/name NCB Tissue HWS was positioned between the two halve fibrous layers which are then joined together to reconstitute the absorbent core.

AGM used was 0.8 g of available from Dow Chemicals (XZ 9589001-cross-linked sodium polyacrylate).

The chitosan-pH buffering wet powder used was the one prepared in Example A at an amount of 0.9 g.

Example F

The feminine pantiliner used in the following examples is a modified panty liner based on Always "Alldays Duo Active" manufactured by Procter & Gamble, Germany. The topsheet is a film/non woven composite {film supplier code BPC 5105 CPM BP Chemical Germany, non-woven supplier code ARBO TB/BI Mequinenza Spain}. The core material is a tissue laminate (13.2 cm×4.0 cm) composed of a 2 layers of air laid tissue of 55 g/m$^2$ basis weight {available from Unikay Italy under the supplier code Unikay 303 LF}. Between the two tissue layers the laminate contains 0.3 g of chitosan and pH buffering means-containing wet powder as described in example A above.

The backsheet comprises two layers a first layer and a second layer. The first layer is in contact with the absorbent tissue and the second layer. The second layer is in contact with the first layer and the undergarment of the wearer. The first layer is a formed apertured film (CPT) made of Low Density PE {supplied by Tredegar Film Products B.V. Holland under the manufacturing code X-1522}. The second layer is composed of a nonwoven laminate {13 MB/16SB manufactured by Corovin GmbH in Germany under the trade name MD 2005}. The nonwoven laminate is composed of 16 g/m$^2$ spun bond and 13 g/m$^2$ meltblown. Each backsheet layer is joined over the full surface by an extensively overlapped spiral glue application at a basis weight of approximately 8 g/m$^2$. The glue utilized for attachment of both backsheet layers was supplied by SAVARE' SpA. Italy (under the material code PM17).

Other panty liners can be made starting from Example F above with similar modifications regarding the incorporation of the chitosan material, pH buffering means and absorbent gelling material as described in Examples B to D above. Typically the solution mentioned in Example B may be used in pantiliner by spraying 7 g thereof and AGM may be used at a level of 0.25 g.

All the above-exemplified pads delivered outstanding odor control properties and fluid handling properties when coming into contact with bodily fluids like menses.

What is claimed is:

1. An article comprising a liquid pervious topaheet, a backsheet, an absorbent core intermediate said backsheet and said topsheet, said absorbent core comprises from about 0.5 g/m$^2$ to about 500 g/m$^2$ of a cationic polysacchariae comprising an aminopolysaccharide selected from the group consisting of chitosan, chitosan salt, crosslinked chitosan and a mixture thereof; and from about 0.1 g/m$^2$ to about 250 g/m$^2$ of an acidic pH buffering means having a pH in the range of from about 3.5 to about 6.5 and comprises a weak acid having its pKa or at least one of its pKas in the range from about 3.5 to about 6.5 and its conjugate base; and from about 5 g/m$^2$ to about 250 g/m$^2$ of absorbent gelling material.

2. An article according to claim 1 wherein said article is a disposable absorbent article selected from the group consisting of a sanitary napkin, a pantiliner, a tampon, a diaper, an incontinent pad, a breast pad, a perspiration pad, an interlabial pad or a body cleaning article.

3. An article according to claim 1 wherein said cationic polysaccharide is selected from the group consisting of chitosan, chitosan salt, crosslinked chitosan and a mixture thereof having a degree of deacetylation of more than 75%.

4. An article according to claim 1 wherein the chitosan salt is selected from the group consisting of citric acid, formic acid, acetic acid, N-acetylglycine, acetylsalicylic acid, tlimaric acid, glycolic acid, iminodiacetic acid, itaconic acid, lactic acid, maleic acid, inalic acid, nicotinic acid, salicylic acid, succinamic acid, succinic acid, ascorbic acid, aspartic acid, glutamic acid, glutaric acid, malonic acid, pyruvic acid, sulfonyldiacetic acid, benzoic acid, epoxysuccinic acid, adipic acid, thiodiacetic acid, thioglycolic acid, alanine, valine, leucine, isaleucine, prolinephenylalanine, tryptofane, methionine, glycine, serine, cysteine, tyrosine, asparagine, glutamine, lysine, arginine, hydroxyproline, pyrrolidone carboxylic acid, chitosonium pyrrolidone carboxylate and mixtures thereof.

5. An article according to claim 1 wherein the pH buffering means is selected from the group consisting of citric acid/sodium hydroxide, citric acid/sodium citrate, citric acid/potassium citrate, oxalic acid/sodium oxalate, taxtaric acid/potassium hydrogen tartarate, oxalic acid/potassium tetra oxalate dihydrate, phthalic acid/potassium phthalate, phthalic acid/sodium phthalate acetic acid/sodium acetate, benzoic acid/sodium benzoate, glutaric acid/sodium glutarate, adipic acid/sodium adipate, carbonic acid/sodium carbonate and mixture thereof axid most preferably is citric acid/sodium citrate, citric acid/sodium hydroxide and/or citric acid/potassium citrate.

6. An article according to claim 1 further comprising an additional odor control agent selected from the group consisting of zeolites, silicates, activated carbons, diatomaceous earth, cyclodextrine, clay, chelating agents, ion exchange resins, perfumes and mixture thereof.

7. An article according to claim 6, wherein the level of the additional odor control agent or a mixture thereof is from about 0.5 $g/m^2$ to about 600 $g/m^2$.

8. A method of controlling odour associated with bodily fluids wherein said bodily fluids are contacted with an odour control system comprising a cationic polysaccharide, selected from the group consisting of chitosan, chitosan salt, crosslinked chitosan and a mixture thereof, and an acid pH buffering means typically having a pH in the range 3.5 to 6.5.

* * * * *